(12) United States Patent
McClain

(10) Patent No.: US 6,409,654 B1
(45) Date of Patent: Jun. 25, 2002

(54) INCUBATOR SYSTEM WITH MONITORING AND COMMUNICATING CAPABILITIES

(76) Inventor: Anthony McClain, 364 Shadetree La., Lawrenceville, GA (US) 30044

( * ) Notice: Subject to any disclaimer, the term of this patent is extended or adjusted under 35 U.S.C. 154(b) by 23 days.

(21) Appl. No.: 09/637,377

(22) Filed: Aug. 15, 2000

(51) Int. Cl.[7] ............................ A61G 11/00; A47C 20/02
(52) U.S. Cl. ............................................. 600/22; 5/655
(58) Field of Search ................................ 5/655; 600/22, 600/301, 300; 177/45; 128/897; 340/573.4; 248/129

(56) References Cited

U.S. PATENT DOCUMENTS

| | | | | |
|---|---|---|---|---|
| 3,858,570 A | * | 1/1975 | Beld et al. | ...................... 600/22 |
| 4,492,279 A | * | 1/1985 | Speckhart | ..................... 177/45 |
| 5,149,030 A | * | 9/1992 | Cockrill | ...................... 248/129 |
| 5,446,934 A | * | 9/1995 | Frazier | .......................... 5/655 |
| 5,687,717 A | * | 11/1997 | Halpern et al. | ............. 600/300 |
| 5,808,552 A | * | 9/1998 | Wiley et al. | ............. 340/573.4 |
| 5,950,630 A | * | 9/1999 | Portwood et al. | ........... 128/897 |
| 5,971,913 A | * | 10/1999 | Niewkirk et al. | ............. 600/22 |
| 6,168,563 B1 | * | 1/2001 | Brown | ....................... 600/301 |

* cited by examiner

Primary Examiner—Eric F. Winakur
Assistant Examiner—Nikita R Veniaminov
(74) Attorney, Agent, or Firm—William B. Noll

(57) ABSTRACT

An incubator, especially adapted for premature infants, and supporting system to control, monitor, and communicate data and images to remote locations. The incubator has been modified by the inclusion of a ventilation system, weight scale, plural cameras, microphone/speaker means, and X-ray means. Externally, the incubator includes a control console, touchscreen display panel with processor and a primary display panel. Operation of the incubator is controlled by a hub interface, a central server and modem, and an internet server with modem.

5 Claims, 2 Drawing Sheets

INCUBATOR SYSTEM WITH MONITORING AND COMMUNICATING CAPABILITIES

FIELD OF THE INVENTION

This invention is directed to the field of incubators, an apparatus in which prematurely born infants are kept and cared for under controlled conditions. More particularly, it relates to an improved incubator system that has monitoring and communicating capabilities.

BACKGROUND OF THE INVENTION

The present invention teaches an incubator system, such as for premature infants, that monitors the infant and its environment, and readily communicates the conditions to a server where patient data and images are passed along to hospital stations, and to the internet for viewing by the patient's doctors and family. Conventional incubators are medical units which provide controlled environments for premature or otherwise delicate or sick infants. The purpose of the incubator is to isolate the infant from the outside atmosphere which might be the source of infections or which might be inadequate to aid the infant in overcoming his/her difficulty.

Infant incubators generally are provided with control means for adjusting the environment within the incubator (i.e., the temperature, humidity, and oxygen content of the atmosphere within the incubator) and display means for indicating the conditions of the environment within the incubator and the condition of an infant positioned within the incubator (i.e., respiration rate and skin temperature). All known incubators have the controls and displays mounted on the front of the base of the incubator and below the hood. This location of the controls and displays is inconvenient to those attending to the care of an infant within the incubator. One must bend down to read the displays and, when the front door of the incubator is open to provide complete access to an infant, one must work around the open front door. In addition, in order to observe the displays which indicate the conditions within the incubator and the condition of the infant, one must be right at the incubator and cannot observe these displays from a remote location.

The prior art teaches a number of improvements to these conventional medical units and related devices to avoid some of the problems noted above. However, other problems were introduced. Nevertheless, the prior art is reflected by the following U.S. Patents:

a.) U.S. Pat. No. 6,011,477, to Teodorescu et al., teaches a monitoring system that includes a first sensor for detecting the respiration and/or movements of an infant and an optional second sensor for detecting the presence and/or movement of the infant or proximal objects surrounding the infant. An optional accelerometric sensor detects movements of a platform supporting the infant and contributes supplementary movement data to the monitoring system. An optional audio sensor detects sounds associated with the infant or proximal objects. None of the sensors are physically attached to the infant. A controller conditions and processes the various sensor signals and generates alarms by interpreting the sensor signals. The controller optionally communicates with a remote control unit. In one embodiment the first sensor signal is filtered to extract respiration- and nonrespiration-related signals that are processed by a signal processor, which compares the extracted signals to thresholds, and if neither signal exceeds its threshold for a predetermined time, a low signal alarm is generated. In another embodiment, the signal processor determines whether a respiration decay period is less than a threshold value, and if not, generates a respiration decay alarm.

b.) U.S. Pat. No. 5,453,077, to Donnelly et al., is directed to an infant thermal support device which provides convective heat transfer similar to an incubator yet which allows for unlimited care provider access to the infant without compromising the infant's thermal environment. The device has an infant support with head and foot ends and lateral sides, and provides a heated curtain of air traveling over an infant on the support to maintain the temperature of the infant at an appropriate level. Vertically oriented curtains of air travel upwardly from the lateral edges and at least one end of the support. The device provides warmth to the infant on the support by virtue of the heated air curtain, and the vertically oriented air curtains reduced perturbations of the heated air curtain caused by physical disturbances adjacent to the device such that a canopy enclosing the device is not required. The device further comprises a raisable and lowerable canopy and infrared heater, such that the device can function as either an infant radiant warmer, an incubator or both. Sensors mounted on the device sense disturbances around the device and the position of the canopy and vary the speeds of the heated air curtain and perturbation reducing curtains accordingly.

c.) U.S. Pat. No. 5,446,934, to Frazier, relates to a baby holding pen or crib, and includes automatic position adjusting, monitoring, and interactive communication means, including alarms, for communicating information to and from the crib or pen from a remote location. Such means include interactive audio and visual means, such as prerecorded messages and preprogrammed tactile simulation. The crib includes a combination of a bed surface that is adjustable in both longitudinal and lateral angles; a heating and cooling means to maintain the crib, area at a comfortable temperature; speakers that play back prerecorded sounds to the baby such as a recording of a mother's soothing voice or instructions to attendants to the location of the crib; visual sensing equipment, such as video monitors, including alarms to remind an attendant of feeding time, diaper changing time, bathing time, or medicine dosage time; and a plurality of sensors, including temperature sensors, vital function sensors, and the like.

d.) U.S. Pat. No. 5,330,415, to Storti et al., teaches an infant incubator in which the controls and displays are provided in a module which is in proximity to but spaced from and above the hood of the incubator at generally the eye-level of a standing adult.

e.) U.S. Pat. No. 5,183,457, to Gatts et al., is directed to an infant environmental transition system which provides an infant with a controlled, healthy transition from an intrauterine environment to the extrauterine environment. The system includes a housing within which the infant is supported by a soft, form-fitting bed. Environmental conditions provided within the housing include simulated motions, sounds and tactile sensations resembling the intrauterine environment. A suspension and drive system controls the degree of movement imparted to the housing and to an infant supported therein. The resulting motion closely approximates the motion experienced by the fetus while the mother is walking. The sound profile simulates intrauterine cardiovascular and gastrointestinal sounds. The system simulates day and night variations in motions and sounds, integrates changes to the environment over time toward the natural extrauterine environment, and may respond to infant activity or other inputs at various intervals.

f.) U.S. Pat. No. 5,006,105, to Sherard, relates to an apparatus setting forth a therapy apparatus for newborn infants, including a cabinet member mounting life monitoring equipment and storage compartments therewithin. The apparatus includes a planar top surface mounting a chamber, with the chamber including transparent side panels and an extensible and contractable cover housing to permit ease of access to the infant, with the housing including slot members hingedly mounted together and securable within opposed lateral tracks. The tracks farther include photo-therapy illumination members extending longitudinally of the slats, and further including a support cushion positionable upon a floor of the cavity.

While the prior art offer some solutions to the need for providing better control of the operating systems for monitoring the environment of an incubator, none present a system for controlling, monitoring and communicating data and images to remote locations, where such a system is so important to the care of a new born infant, for example. The manner by which the present invention achieves these goals will become more apparent from the description which follows, particularly to those skilled in the art.

SUMMARY OF THE INVENTION

The present invention is directed to the combination of an incubator and a system for controlling, monitoring and communicating data and images to remote locations. The combination includes an incubator having a transparent enclosure adapted to receive an infant supporting means in a controlled environment. The system within the incubator includes a ventilating system, operable by a fan and motor, to control the atmospheric environment within the enclosure, a weight scale to monitor changes in weight of the infant, a pair of cameras trained at different angles on the infant. a microphone/speaker system for transmitting sounds into and out of said incubator, and an on site x-ray means. Externally, the incubator features a control console, a touch-screen display panel with processor to control various functions of the incubator, and a primary display panel to monitor functions within the incubator. Finally, in communication with the internal components and external features is a hub interface, a central station server having a modem, and an internet server having a second modem in communication with the central station server. Further, the second modem is in communication with a world wide internet system for pictorial accessing images and data from the incubator.

Accordingly, an object of this invention is to provide an improved incubator system, such as for the handling of premature infants, where the incubator includes means for monitoring, controlling and easy communication with the environment of the incubator for medical personnel and family.

A further object hereof is the provision of including plural cameras within the incubator to allow receipt of images therefrom.

Still another object of the invention lies in the incorporation of an integrated weight scale to weigh the infant without disturbing the infant nor altering its environment.

Another object lies in the incorporation of x-ray means within the incubator.

These and other objects will become apparent to those skilled in the art from the description which follows.

DETAILED DESCRIPTION OF PREFERRED EMBODIMENT

Figure 1:
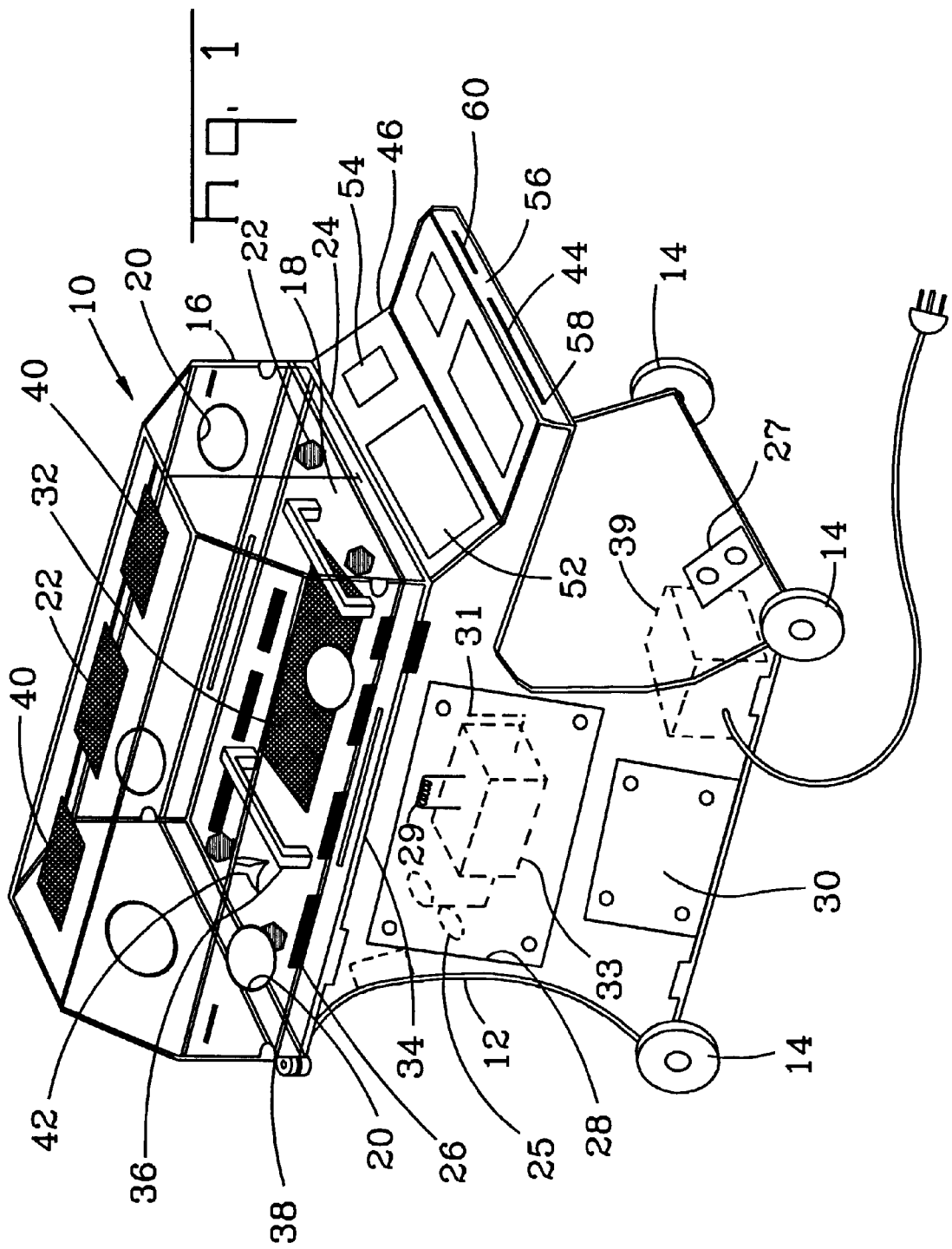
FIG. 1 is a perspective view of an exemplary incubator, such as for a premature infant, incorporating the system of this invention to control, monitor and communicate data and images from the incubator to remote locations.

The invention relates to the combination of an incubator, such as for a premature infant, and a system for controlling and monitoring conditions within the incubator, and for communicating data and images from the incubator to remote locations. The invention will now be described with regard to the two Figures where like reference numerals represent like components or features in the two views.

Turning first to FIG. 1 which illustrates a conventional incubator 10 with various modifications according to this invention. The incubator 10 comprises mobile base 12, preferably on a series of rollers 14, a transparent enclosure 16, and a support floor 18 for receiving a pad (not shown) upon which the infant rests. Access portals 20, preferably four in number, are provided to allow access to the infant without altering the environment of the incubator or introducing germs to the interior. Further, lights 22 may be included for the interior of the incubator. The incubator 10 may be provided with a temperature probe port 24.

Since controlled temperature is vital to the life of the infant, an air conditioning or ventilation system is included. Such a system, positioned within the base 12, includes a fan and motor 25, as known in the art, air vents 26, heating coil 29, thermal probes 31, controlled by a Controller/CPU/Plug 33, and a standard 120 VAC output 27, preferably rated at about 12–15 Amps max. Since noise can be a problem, particularly for a new infant, an active noise cancellation circuit may be included. The active noise cancellation system will keep the infant from being bothered by the noise output from the fan/motor. Further, the active noise cancellation system will monitor the decibel noise output, and once the db output reaches a threshold level, the incubator will create a work order and send it to hospital personnel to have the fan/motor replaced. In any case, to access internal components in the base, a pair of removable panels 28, 30 may be provided.

Internally, the incubator has been modified by the inclusion of an X-ray plate 32 and X-ray cassette 34. Further, a weight scale 36 is included to allow periodic weighing of the infant without disturbing the infant, or removing him/her from the controlled environment. Also, since it may be necessary to elevate the infant, a bed mount 38, operable from about 0 to 25 degrees may be incorporated into the incubator. Further, as a back up power means, a battery 39 may be included, especially if it's necessary to move the incubator.

Since a feature of the invention is to allow imaging access to the infant from a remote location, preferably a pair of cameras 40 are included along the top to cover different angles of the infant for transmission as later described. Music is known to have a soothing effect on small children and infants, a combination microphone/speaker 42 can be included to pipe in soft music, as may be provided by a CD-ROM drive 44, or to monitor sounds from the infant.

Externally the incubator is provided with a generally, lateral extending member 46 on which are mounted a control panels 48, and keyboard 50, an LLD touchscreen display/CPU panel 52, and a secondary LLD display panel 54. For convenience, the edge 56 of extending member 46 may include slots 58, 60 for inserting the CD-Rom and 3.5" floppy disk, respectively.

Figure 2:
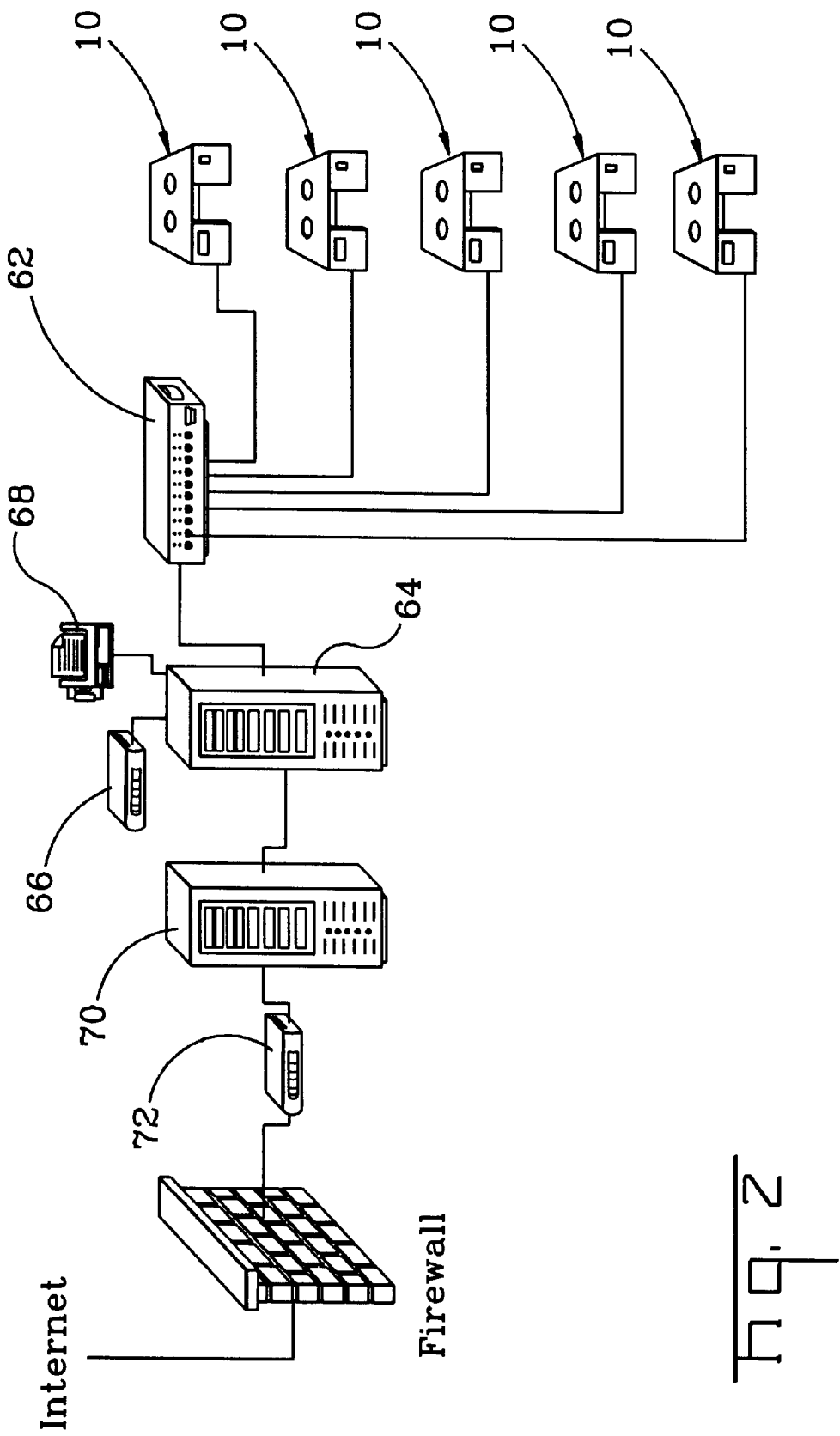
FIG. 2 is a simplified pictorial and block diagram of the monitoring and communicating system of this invention.

FIG. 2 illustrates pictorially the network layout for controlling, monitoring and effecting communication between the plural incubator and remote locations. The system hereof, by the use of supporting software, as known in the art, includes a hub interface 62 in communication with the plural incubators 10, a first central station server 64 having a modem 66 and fax machine 68, where the latter may be used to transmit instructions, data, etc. to selected personnel regarding data from the incubators 10. Additionally, a second internet server 70 is provided, through a modem 72, to transmit images, data, etc. to friends, family and medical personnel at locations, whether it be at home or within the hospital, remote from the respective incubators.

By the arrangement above, the incubator 10 will monitor the temperature of the infant, as well as the environment surrounding the infant. In addition, the system will monitor itself for problems or malfunctions. Using artificial intelligence, the incubator 10 will offer suggestions to hospital or technical personnel in case of a failure. In such a case, the incubator will automatically generate a work order on the hard drive of the controller 33, with the option to automatically fax the work order to selected personnel. The incubator will also have the ability to automatically page such selected personnel in case of a major system failure via the central station server 62.

It is recognized that variations, modifications and changes may be made to the system of this invention without departing from the spirit and scope of the invention, particularly by those skilled in the art. Accordingly, no limitation is intended to be imposed thereon except as set forth in the following claims.

What is claimed is:

1. In combination with an incubator having a transparent enclosure adapted to receive an infant supporting means in a controlled environment, a system for controlling, monitoring and communicating data and images to remote locations, the system comprising:
 a.) within said incubator,
  i.) a ventilating system, operable by a fan and motor, to control the atmospheric environment within the enclosure, including control means for monitoring a threshold level of noise from said fan and said motor, whereby said threshold level is reached a signal will be generated to monitoring personnel of the malfunction;
  ii.) a weight scale to monitor changes in weight of the infant;
  iii.) a pair of cameras trained at different angles on the infant;
  iv.) a microphone/speaker system for transmitting sounds into and out of said incubator;
  v.) an on site X-ray means;
 b.) externally of said incubator,
  i.) a control console;
  ii.) a touchscreen display panel with processor to control various functions of the incubator,
  iii.) a primary display panel to monitor functions within the incubator; and
 c.) means remote from said incubator in communication through a hub interface with said components within said incubator and externally of said incubator, where said means include
  i.) a central station server having a modem;
  ii.) an internet server having a second modem in communication with said central station server, where said second modem is in further communication with a world wide internet system for pictorially accessing images from said incubator.

2. The combination system according to claim 1, wherein said hub interface is a LAN system allowing for wireless communication.

3. The combination system according to claim 1, wherein said incubator includes a portable power source to provide portable mobility to the incubator.

4. The combination system according to claim 1, including voice feedback means for allowing communication between medical personnel.

5. The combination system according to claim 1, including a fax machine in electrical communication with said central station server, whereby data can be transmitted there through to selected personnel.

* * * * *